US00PP30711P2

(12) United States Plant Patent
Hansen

(10) Patent No.: US PP30,711 P2
(45) Date of Patent: Jul. 16, 2019

(54) ***BUDDLEIA* PLANT NAMED 'PINK CASCADE'**

(50) Latin Name: *Buddleia davidii*
Varietal Denomination: Pink Cascade

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,743

(22) Filed: Apr. 18, 2018

(51) Int. Cl.
*A01H 5/02* (2018.01)
*A01H 6/30* (2018.01)

(52) U.S. Cl.
USPC ..... Plt./242

(58) Field of Classification Search
USPC ..... Plt./242, 263.1
CPC ... A01H 5/02; A01H 5/00; A01H 5/08; A01H 5/0812; A01H 6/30
See application file for complete search history.

(56) References Cited

PUBLICATIONS

Plant Delight Blog 2017, New Cascades Butterfly Bushes . . . not your grandmothers *Buddleias*, retrieved on Mar. 25, 2019, retrieved from the Internet at http://blog.plantdelights.com/new-cascade-butterfly-bushes-not-your-grandmothers-buddleias/, 4 pp. (Year: 2017).*

* cited by examiner

*Primary Examiner* — June Hwu

(57) ABSTRACT

The new and distinct plant of *Buddleia* 'Pink Cascade' is a rounded-mounded, multi-stemmed, winter-hardy butterfly bush with very long, narrow, slightly drooping flowering thyrse producing a waterfall effect over a long season beginning mid-summer with sweetly-fragrant flowers of medium pink petals that are attractively offset by dark green foliage with silvery undersides. The new plant is valuable for landscaping en masse, as an accent or as a potted specimen.

1 Drawing Sheet

Botanical classification: *Buddleia davidii.*
Variety denomination: 'Pink Cascade'.

BACKGROUND OF THE PLANT

The present invention relates to the new and distinct butterfly bush plant of the Scrophulariaceae family, *Buddleia* 'Pink Cascade' hybridized by Hans A. Hansen in the summer of 2013 at a wholesale perennial nursery in Zeeland, Mich., USA. 'Pink Cascade' is the result of an ongoing breeding program conducted by the inventor. The goals for this program have been to produce improved, garden-worthy plants for the ornamental plant market. The new plant, assigned the breeder code 13-9-2 toward the end of the evaluation trials was the result of a single seedling selection from a cross between the unreleased proprietary hybrid 12-89-01 (not patented) as the female or seed parent. The male parent was an unreleased proprietary hybrid with the in-house name of "cascading lilac." The new cultivar was selected as single individual flowering plant within the progeny of the above cross at the same nursery in Zeeland, Mich.

No plants of *Buddleia* 'Pink Cascade' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

*Buddleia* 'Pink Cascade' was first asexually propagated from a single select plant in 2015 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

In comparison to the new plant the female parent has a deeper pink flower color and is upright in habit. The male plant has shorter, extremely pendulous habit and lilac-purple flowers compared with the medium pink flowers of the new plant.

The nearest comparison plants known to the inventor are *Buddleia* 'Pink Delight' (not patented), 'Pink Pagoda' U.S. Plant Pat. No. 23,214, 'Wisteria Lane' U.S. Plant Pat. No. 27,833, and the two co-pending applications from the same inventor (U.S. Plant patent application Ser. No. 15/932,773) and 'Lavender Cascade' (U.S. Plant patent application Ser. No. 15/932,774). 'Pink Delight' is a slightly larger plant in habit and smaller in thyrse size and has more glaucous grey foliage. 'Pink Pagoda' is shorter and narrower in habit with much smaller thyrse having flowers of a different hue with more brightness. 'Wisteria Lane' is shorter in habit with smaller thyrse and the branches are more drooping instead of mainly the thyrse drooping and the petals are light purple. 'Grand Cascade' is larger in habit and has longer and broader thyrse with petals that are different colored. 'Lavender Cascade' has taller and broader habit and flower petals that are light purple with less pinkish hue.

*Buddleia* 'Pink Cascade' is a unique winter-hardy butterfly bush different from all other *Buddleia* cultivars known to the inventor based on the following combined repeatedly observed distinguishing traits:

1. Winter-hardy butterfly bush shrub, with multiple-stemmed, well-branched, rounded, waterfall-type arching, mounded habit.
2. Large, narrow, many-flowered, elongated and slightly-drooping thyrse flowering over a prolonged season beginning mid-summer.
3. Flowers with medium pink petals.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
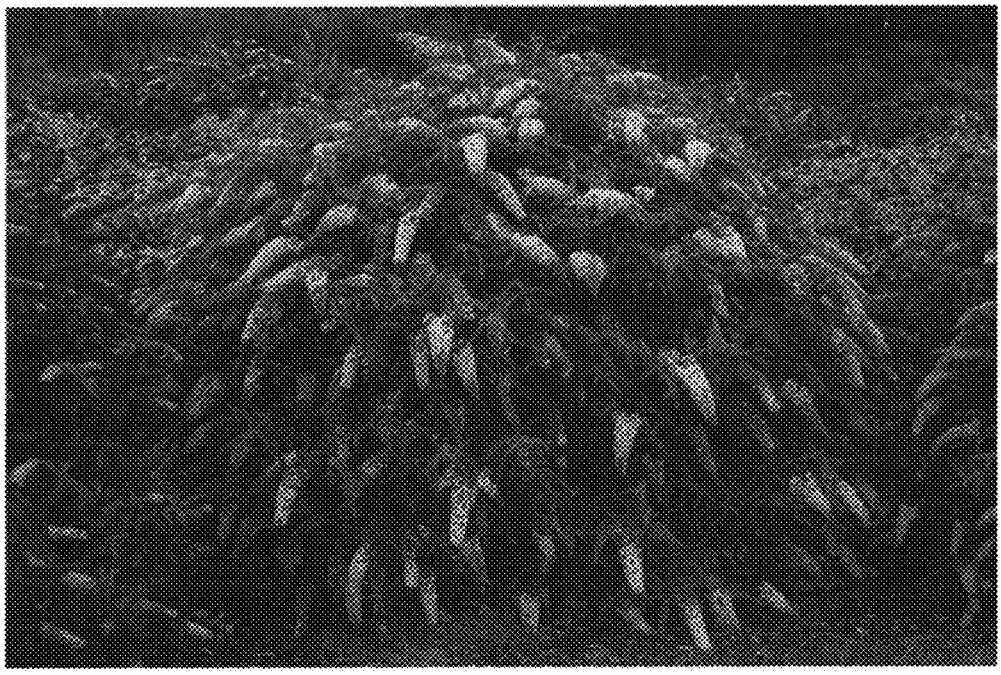
FIG. 1 shows the habit of a four-year-old plant in mid-season flowering.
Figure 2:
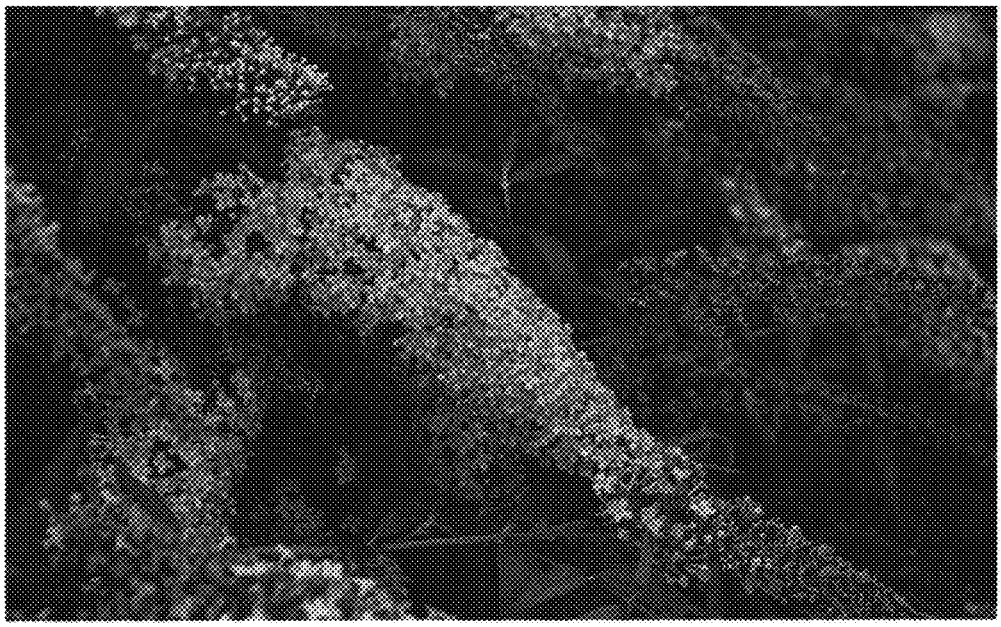
FIG. 2 shows a close-up of the inflorescence.

The following descriptions and color references are based on the 2015 edition of The Royal Horticultural Society Colour Chart except where common dictionary terms are used. The new plant, *Buddleia* 'Pink Cascade', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 12-89-01 (not patented) as the female or seed patent; the male or pollen parent was an unreleased proprietary hybrid known by the in-house name of "cascading lilac;".

Propagation:

*Method.*—Softwood shoot cuttings.

*Time to initiate roots from tissue culture.*—About two weeks.

*Rooting habit.*—Normal, dense and branching, developing thick at base to about 1.5 cm diameter.

*Root color.*—Creamy white between RHS 159A and lighter than RHS 159 D depending on soil type.

*Crop time.*—Under normal summer growing conditions 12 to 15 weeks to flower in a four-liter container from cutting. Plant vigor is very good.

Plant description:

*Plant shape and habit.*—Winter-hardy, herbaceous to semi-woody, well-branched shrub with about 20 thick upright and branched main stems producing a rounded mound, to about 162 cm tall and about 275 cm wide.

*Stem.*—Terete and woody in lower portion, with exfoliating bark; younger upper portion tomentose to tomentulose; strong and flexible, arching or drooping especially in terminal thyrse; average about 150 cm tall from soil line to just below terminal flowers, and about 20.0 mm diameter at the base; about 24 branches per main stem before distal flowers in upper 12 nodes, extending at about 45° angle from main stem.

*Stem color.*—Young distal portion just below flowers nearest RHS 148D; basal 15 cm between RHS 200C and RHS 165B with striations between RHS 200A and RHS N199B.

*Internode.*—About 18 nodes per main stem below terminal thyrse, average internode length about 8.0 cm on unpinched plant; upper internodes slightly more elongated than lower internodes.

Foliage description: Opposite; lanceolate; decussate; serrate with about two teeth per cm, teeth about 1.0 mm long and 1.5 mm wide; young expanding leaves puberulent abaxial and adaxial, becoming glabrous adaxial; attenuate to cuneate base and narrowly acute apex; no foliar fragrance detected;

*Leaf blade size.*—Up to about 10.0 cm long and about 20.0 mm wide, average about 9.2 cm long and about 18.0 mm wide; becoming smaller in distal portion of stem.

*Foliage color.*—Young expanding leaf adaxial nearest RHS 189A, young expanding abaxial nearest RHS 191C; mature leaves adaxial nearest and RHS 139A, mature abaxial between RHS 189B and RHS 189C.

*Veins.*—Reticulate; abaxial costate, puberulent; adaxial glabrous, slightly impressed.

*Vein color.*—Young abaxial midrib and secondary veins nearest RHS 194D, young adaxial midrib and secondary veins nearest RHS 145C; mature abaxial midrib and secondary veins nearest RHS 194D and adaxial midrib and secondary veins nearest RHS 139A.

*Petioles.*—Short; about 3.5 mm long and 2.5 mm wide.

*Petiole color.*—Adaxial nearest RHS 138A and abaxial nearest RHS 146D.

*Inflorescence description.*—Glomerate thyrse consisting of about 1,000 to 2,000 self-cleaning salverform flowers; to about 34.5 cm long and 10.0 cm wide at base; average about 33.0 cm long and 9.5 cm wide; beginning in mid-July and continuing until frost in Michigan; thyrse effective for about three weeks.

*Inflorescence attitude.*—Slightly drooping.

*Flower buds.*—Elongated clavate, apex rounded; one day prior to opening about 13.5 mm long, about 3.5 mm diameter in club, tube about 1.0 mm diameter and about 8.0 mm long.

*Flower bud color.*—Nearest RHS 70B in club portion, tube blend between RHS 39C and RHS 70C.

*Sepals.*—Typically four, rarely five; forming campanulate calyx; adpressed to corolla tube; acute apex; glabrous adaxial and pubescent abaxial; margin entire; fused in about the basal 2.0 mm and split in about the terminal 0.5 mm, individually less than about 1.0 mm wide at point of fusion; forming a corolla about 2.5 mm long and about 1.0 mm across.

*Sepal color*.—Adaxial and abaxial nearest RHS 138A.

*Flowers*.—Salverform; actinomorphic; perfect; to about 12.0 mm long and 10.0 mm wide at face; with straight terete tube about 9.0 mm long and 1.0 mm diameter, and a abruptly applanate face about 10.0 mm across; attitude outward from thyrse center; remaining on the thyrse and effective for about five to seven days.

*Flowers fragrance*.—Pleasantly and distinctly sweet.

*Petals*.—Typically four; glabrous abaxial and on adaxial blades and tube, puberulent center abaxial tube; blade rounded with crenate margin; apex rounded; blade to about 3.5 mm across and about 4.5 mm long from throat to apex.

*Petal color*.—Upon opening and when fully open adaxial tube base nearest RHS NN155D, distal tube and throat nearest RHS 23A, adaxial face blade nearest RHS N74D; upon opening and when fully open abaxial tube base nearest RHS NN155D, distal tube blend between RHS 39C and RHS 70C, and abaxial petal blades nearest RHS N74D; adaxial and abaxial petal face becoming nearest RHS 75B with age.

*Gynoecium*.—Pistil: one; about 4.0 mm long; Style: glabrous, glutinous, ellipsoidal; about 1.0 mm long and about 0.5 mm diameter; color nearest RHS 145B; Stigma: narrow ellipsoidal, minutely puberulent; about 0.2 mm in diameter and about 1.5 mm long; color nearest RHS 145A; Ovary: superior; ellipsoidal; about 1.0 mm across at base and 1.5 mm tall; distally tapering to style; color nearest RHS 146D.

*Androecium*.—Typically four; Filaments: short or less than 0.5 mm long and less than 0.1 mm diameter; adnate to middle of adaxial corolla tube; color nearest RHS NN155D; Anthers: typically four; ellipsoidal; introrse; about 1.2 mm long and 0.5 mm wide; color nearest RHS 11D; Pollen: globose, less than 0.1 mm long; color nearest RHS 11D.

*Pedicel*.—Short, puberulent; about 2.0 mm long and about 0.3 mm diameter; color nearest RHS 138A.

*Peduncle*.—Quadrangular; tomentulose to tomentose, flexible and strong; to about 35.0 cm long, and about 3.0 mm across at base below flowers.

*Peduncle color*.—Nearest RHS 146D with portions in high sun blushed with nearest RHS 176C.

*Fruit*.—Moderate to heavy fruit set; oblong with acute apex; attenuate base; glabrous, bi-valved, septicidal capsule; about 9.0 mm long and about 1.8 mm diameter toward apex and 1.0 mm toward base.

*Fruit color*.—As maturing nearest RHS 187A; when mature and dehiscing nearest RHS 164B.

*Seed*.—Elongated linear with sharply acute ends; about 1.5 mm long and less than 0.2 mm across in center.

*Seed color*.—Nearest RHS 200A.

Disease resistance: Resistance has been noted to deer browsing. Other pest and disease resistance beyond that common to butterfly bush cultivars has not been observed. The plant grows best with plenty of moisture and adequate drainage, but is able to tolerate some drought when mature.

Hardiness at least from USDA zone 6 through 10 with some occasional stem dieback.

It is claimed:

1. A new cultivar of winter-hardy butterfly bush plant named *Buddleia* 'Pink Cascade' as herein illustrated and described.

* * * * *